United States Patent
Kondo et al.

[11] Patent Number: 6,136,337
[45] Date of Patent: Oct. 24, 2000

[54] LONG-LASTING COMPOSITION FOR RECTAL ADMINISTRATION

[75] Inventors: Osamu Kondo; Tomoko Fujimori; Shigeo Tanaka; Fumio Urushizaki, all of Tokyo, Japan

[73] Assignee: Taisho Pharmaceutical Co., Ltd., Japan

[21] Appl. No.: 09/029,624

[22] PCT Filed: Sep. 4, 1996

[86] PCT No.: PCT/JP96/02497

§ 371 Date: Jul. 8, 1998

§ 102(e) Date: Jul. 8, 1998

[87] PCT Pub. No.: WO97/09035

PCT Pub. Date: Mar. 13, 1997

[30] Foreign Application Priority Data

Sep. 7, 1995 [JP] Japan ................................ 7-230151

[51] Int. Cl.[7] .................................................. A61F 9/02
[52] U.S. Cl. .................................. 424/436; 424/DIG. 15; 514/966
[58] Field of Search .......................... 424/436, DIG. 15; 514/966

[56] References Cited

U.S. PATENT DOCUMENTS 4,292,300  9/1981  Byrne et al. .............................. 424/19

FOREIGN PATENT DOCUMENTS

| 103995 | 8/1983 | European Pat. Off. . |
|---|---|---|
| 54-26325 | 2/1979 | Japan . |
| 63280016 | 11/1983 | Japan . |
| 59-55817 | 3/1984 | Japan . |
| 61-109710 | 5/1986 | Japan . |
| 1143825 | 6/1989 | Japan . |
| 215024 | 1/1990 | Japan . |
| 4164023 | 6/1992 | Japan . |
| 640889 | 2/1994 | Japan . |

OTHER PUBLICATIONS

Webster's II new Riverside University Distionary, p 75.

Chemical Abstracts, vol. 124, No. 12 Mar. 18, 1996 # 156068.

*Primary Examiner*—Carlos A. Azpuru
*Attorney, Agent, or Firm*—Lorusso & Loud

[57] ABSTRACT

There is provided a composition for rectal administration suitable for curing hemorrhoids or the like by which the concentration of a medicine in the affected tissue is increased and the potency of the medicine is expected to continue. The long acting composition for rectal administration includes an acrylic acid polymer, a vasoconstrictor and a rectal tissue-curing agent.

4 Claims, 2 Drawing Sheets

LONG-LASTING COMPOSITION FOR RECTAL ADMINISTRATION

This application is a 371 continuation of PCT/JP96/02497 filed Sep. 4, 1996, which is a continuation of JP07-230151 filed Sep. 7, 1995.

BACKGROUND OF THE INVENTION

1. Field of the Invention

This invention relates to a composition for rectal administration, more particularly to a composition for rectal administration suitable for local curing such as curing of hemorrhoids or the like, which composition comprises an acrylic acid polymer, a vasoconstrictor and a rectal tissue-curing agent, with which the concentration of the curing agent in the rectal tissue is increased and the potency of the curing agent continues so as to be "long acting."

2. Background Art

It is known that conventional preparations for rectal administration, such as a suppository and the like, when administered to an anorectal region, spread with time from the administered site to the upper region of the rectum because a base in the preparation is melted at the body temperature to become a liquid state. For the purpose of local curing, such as curing of hemorrhoids or the like, the spreading of the preparation to the upper region of the rectum results in a decrease in the amount of the preparation present in the vicinity of the affected region. Therefore, reports have been made on innovations in preparations for rectal administration for the purpose of preventing the spread of the preparation in the rectum and allowing the preparation to remain in the vicinity of the affected region.

For example, JP-A-54-26325 discloses a preparation for rectal administration which remains in the vicinity of the affected region of the rectum and which contains a metal salt of polyacrylic acid. A mixture of polyacrylic acid and polyvinylpyrrolidone for such a purpose is disclosed in JP-A-6-40889 and the use of a carboxyvinyl polymer for such a purpose is disclosed in JP-A-63-280016 and JP-A-1-143825.

SUMMARY OF THE INVENTION

The present inventors have made various studies of compositions for rectal administration and have consequently found that a preparation in the form of a composition comprising an acrylic acid polymer, a vasoconstrictor and a rectal tissue-curing agent not only remains in the vicinity of the affected region in the rectum but also inhibits the curing agent from diffusing from the rectal tissue, increases the concentration of the curing agent in the tissue and has long acting potency.

That is to say, this invention is a long acting composition for rectal administration which comprises an acrylic acid polymer, a vasoconstrictor and a rectal tissue-curing agent.

DESCRIPTION OF THE PREFERRED EMBODIMENTS

Figure 1:
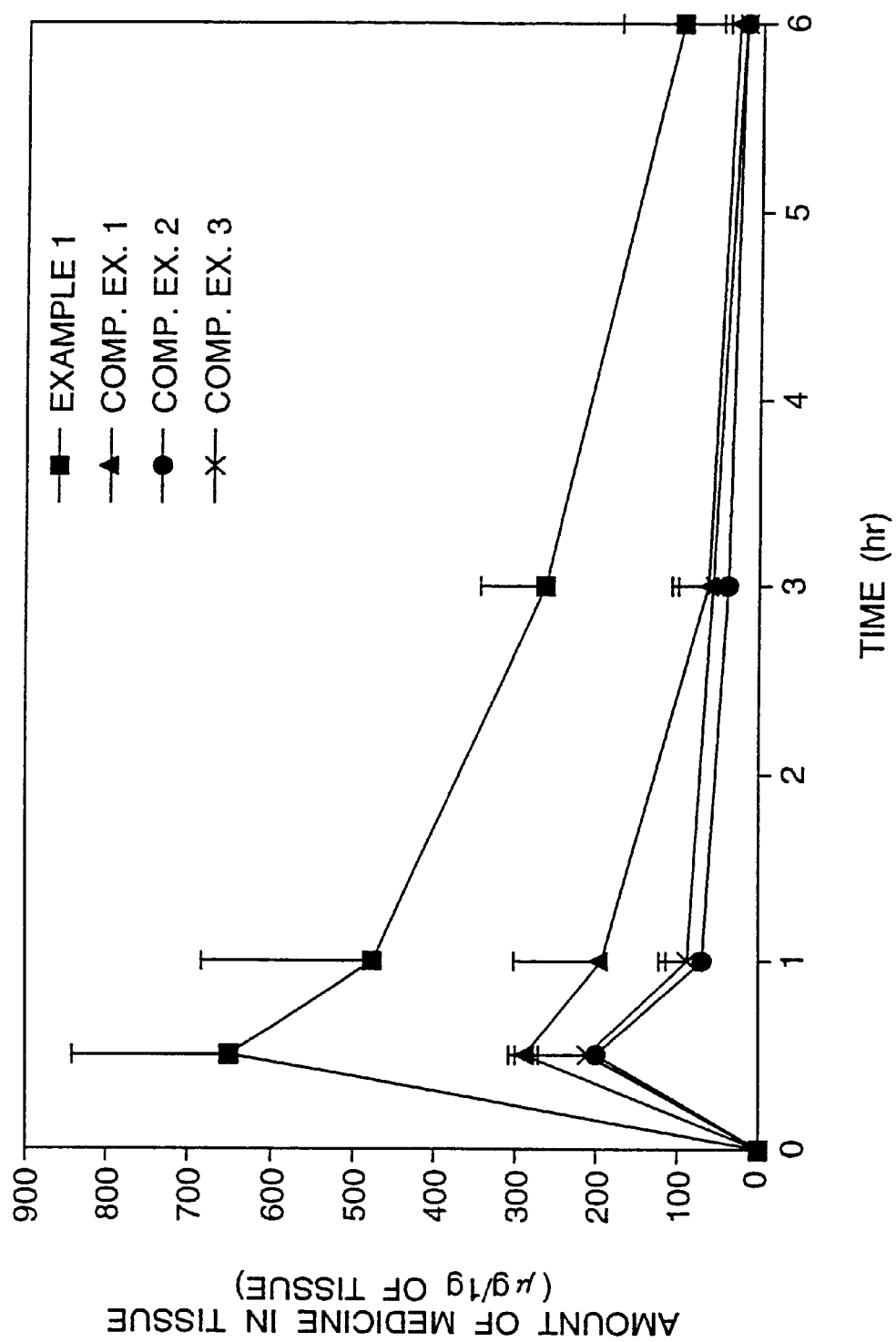
FIG. 1 is a graph showing the results of determination of the amount of lidocaine in 1 g of rectal tissue of a section of 10 cm from the anal region.

In this invention, the terminology "acrylic acid polymer" means a polyacrylic acid, a polyacrylic acid salt, a partially cross-linked polyacrylic acid or its salt. The average molecular weight thereof is 100,000 to 10,000,000 and the content of carboxyl group thereof is preferably 50 to 70%, more preferably 58 to 63%. The particle size is preferably 500 microns or less, more preferably 250 microns or less. Suitable partially cross-linked polyacrylic acids, include, for example, carboxyvinyl polymer, carbomer and polycarbofil, and preferably carboxyvinyl polymer. As a salt of polyacrylic acid, there are mentioned alkali metal salts such as sodium salt, potassium salt and the like; alkaline earth metal salts such as calcium salt and the like; trivalent metal salts such as aluminum salt and the like; and ammonium salt. Preferable are potassium polyacrylate, sodium polyacrylate, calcium polyacrylate and ammonium polyacrylate.

The amount of the acrylic acid polymer formulated is 0.1 to 20% by weight based on the total amount of the composition for rectal administration. Among the acrylic acid polymers, most preferable is carboxyvinyl polymer and the amount of the same formulated is 0.2 to 15% by weight, more preferably 1 to 10% by weight, based on the total amount of the composition for rectal administration.

When the amount of the acrylic acid polymer formulated is small, the duration in rectum becomes poor and when the amount is large, the viscosity becomes high and the production of the preparation and filling with the preparation tend to become difficult.

The term "vasoconstrictor" as used herein means a medicine having a vasoconstrictive action, and may be, for example, tetrahydrozoline hydrochloride, naphazoline hydrochloride, phenylephrine hydrochloride, ephedrine hydrochloride or oxymetazoline hydrochloride. The amount of the vasoconstrictor is 0.005 to 2.0% by weight based on the total amount of the composition for rectal administration. Among the vasoconstrictors, preferable are tetrahydrozoline hydrochloride, naphazoline hydrochloride or oxymetazoline hydrochloride, and the amount of the same is 0.005 to 0.1% by weight based on the total amount of the composition for rectal administration. Among these vasoconstrictors, most preferable is tetrahydrozoline hydrochloride.

The rectal tissue-curing agent is, for example, a medicine which is used for curing hemorrhoids or rectal cancer, and may be, for example, a steroid preparation such as hydrocortisone, hydrocortisone acetate, prednisolone, prednisolone acetate, dexamethasone, dexamethasone acetate, diflucortolone valerate or hydrocortisone propionate butyrate; an anti-phlogistic such as indometacin, ketoprofen, diclofenac sodium, lysozyme chloride or glycyrrhetic acid; a local anesthetic such as ethyl aminobenzoate, lidocaine, lidocaine hydrochloride, dibucaine, dibucaine hydrochloride, procaine, procaine hydrochloride, mepryl-caine hydrochloride or mepivacaine; an antineoplastic agent such as 5-fluorouracil or futraful; an astringent such as zinc oxide, tannic acid, albumin tannate or potassium aluminum sulfate; an antihistamine such as diphenhydramine, diphenhydramine hydrochloride or chlorpheniramine maleate; a wound healing maleate accelerator such as allantoin or aluminum chlorohydroxy-allantoinate; a microbicide such as chlorhexidine hydrochloride, cetrimide, dequalinium chloride and benzalkonium chloride; a sulfa drug such as sulfisomidine, sulfisomidine sodium, homosulfamine or sulfadiazine; vitamins such as cod liver oil, ergocalciferol, riboflavin, pyridoxine hydrochloride or tocopherol acetate; a refrigerant such as d-camphor, dl-camphor, 1-menthol, dl-menthol, mentha oil or eucalyptus oil.

The composition for rectal administration is used, for example, as a suppository or an injection type ointment.

When it is formed into a suppository, a base which is generally used as a suppository base is used. For example, an oleophilic base or a hydrophilic base can be used, or both of them may be used in admixture. Oleophilic bases which may be mentioned include, for example, cacao butter, lanolin fat and hard fat. Suitable hard fats include, for example, Witepsol (manufactured by Hüls), Saposyer (manufactured by Gattefosse), Isocacao (manufactured by Kao) and Pharma sol (manufactured by NOF). The hydrophilic base may be, for example, Macrogol.

The injection type ointment is used in any form, e.g., an oily ointment, a cream or a gel. In this case, the base is a conventionally used base. For example, an oily base, a water-soluble base or a mixture thereof is used, depending upon the form of the oily ointment, cream or gel. Suitable oily bases include, for example, oils and fats, fatty acids, higher alcohols and fatty acid triglycerides. Suitable oils and fats include, for example, olive oil, soybean oil, jojoba oil, rape seed oil, peanut oil, castor oil, mentha oil, coconut oil, cacao oil, palm oil, sesame oil, camellia oil, corn oil, hydrogenated oil, Japan wax, carnauba wax, lanolin oil, bees wax, squalane, squalene, beef tallow, lard, egg yolk oil, spermaceti, fluid paraffin, paraffin and vaseline. Suitable fatty acids include, for example, oleic acid, palmitic acid and stearic acid. As suitable higher alcohols, there can be mentioned, for example, cetanol and stearyl alcohol. A suitable fatty acid triglyceride is, for example, Panasate (manufactured by NOF). Suitable water-soluble bases include, for example, glycerine and propylene glycol.

Moreover, if necessary, surface active agents and additives can be added. Any surface active agent such as anionic, cationic, nonionic or amphoteric surfactant can be used, for example, sorbitan fatty acid esters, glycerine fatty acid esters, decaglin, polysorbate, polyoxyethylene hydrogenated castor oil, polyethylene glycol fatty acid esters, polyoxyethylene alkyl ethers, alkylsulfuric acid salts, alkylammonium salts, N-acylamino acid salts or lecithin. As the alkylsulfuric acid salts, for example, sodium dodecylsulfate may be used. As the alkylammonium salt, for example, stearyltrimethylammonium chloride may be used. Suitable additives include, for example, an antiseptic, an inorganic oxide, a gelling agent, an antioxidant and a pH-regulator. Suitable antiseptics include, for example, alkyl polyoxybenzoates, sorbic acid and chlorhexidine gluconate. Suitable as the inorganic oxide are, for example, light anhydrous silicic acid and titanium oxide. The gelling agent may be, for example, a dextrin fatty acid ester. The antioxidant may be, for example, dibutylhydroxytoluene. Suitable pH-regulators include, for example, citric acid and tartaric acid.

The composition for rectal administration of this invention can be prepared by heating a base which is a soluble component to melt the same, thereafter mixing therewith an acrylic acid polymer, a vasoconstrictor and a rectal tissue-curing agent, and, if necessary, dispersing or dissolving other compounding agents in the base and then cooling them with stirring.

The composition for rectal administration of this invention comprises an acrylic acid polymer, a vasoconstrictor and a rectal tissue-curing agent, by which the durability of the above curing agent is enhanced. The composition has a superior curative effect on diseases for which local action is appropriate, such as hemorrhoids and the like and is useful as a preparation for rectal administration.

Examples and Test Examples are shown below to explain this invention in detail.

EXAMPLE 1

Composition

| | |
|---|---|
| Tetrahydrozoline hydrochloride | 1 g |
| Lidocaine | 60 g |
| Hydrocortisone acetate | 5 g |
| Allantoin | 20 g |
| Tocopherol acetate | 60 g |
| Light anhydrous silicic acid | 20 g |
| Carboxyvinyl polymer | 75 g |
| Witepsol W35 | 1,409 g |

Production Process

In a suppository base (Witepsol W35) which was heated and melted (50° C.–70° C.) were dispersed successively the other components with stirring and they were cooled to about 40° C., after which a suppository container was filled therewith, further cooled and shaped to obtain a suppository.

EXAMPLE 2

Composition

| | |
|---|---|
| Phenylephrine hydrochloride | 5 g |
| Dibucaine | 10 g |
| Hydrocortisone acetate | 5 g |
| Zinc oxide | 100 g |
| Light anhydrous silicic acid | 30 g |
| Carboxyvinyl polymer | 150 g |
| Witepsol H15 | 1,450 g |

Production Process

A suppository was obtained in the same manner as in Example 1.

EXAMPLE 3

Composition

| | |
|---|---|
| Naphazoline hydrochloride | 1 g |
| Lidocaine | 60 g |
| Prednisolone acetate | 1 g |
| Allantoin | 20 g |
| Tocopherol acetate | 60 g |
| Carboxyvinyl polymer | 80 g |
| Witepsol H15 | 1,528 g |

Production Process

A suppository was obtained in the same manner as in Example 1.

EXAMPLE 4

Composition

| | |
|---|---|
| Oxymetazoline hydrochloride | 1 g |
| Lidocaine | 50 g |
| Hydrocortisone acetate | 5 g |
| Diphenhydramine hydrochloride | 5 g |
| Zinc oxide | 100 g |
| Polycarbofil calcium | 100 g |
| Pharma sol B115 | 1,539 g |

Production Process

A suppository was obtained in the same manner as in Example 1.

EXAMPLE 5
Composition

| | |
|---|---|
| Oxymetazoline hydrochloride | 1 g |
| Lidocaine hydrochloride | 60 g |
| Allantoin | 20 g |
| Chlorpheniramine maleate | 4 g |
| Polycarbofil | 75 g |
| Light anhydrous silicic acid | 20 g |
| Pharma sol B115 | 1,520 g |

Production Process

A suppository was obtained in the same manner as in Example 1.

EXAMPLE 6
Composition

| | |
|---|---|
| Tetrahydrozoline hydrochloride | 1 g |
| 5-Fluorouracil | 100 g |
| Carboxyvinyl polymer | 75 g |
| Light anhydrous silicic acid | 24 g |
| Pharma sol B115 | 1,200 g |

Production Process

A suppository was obtained in the same manner as in Example 1.

EXAMPLE 7
Composition

| | |
|---|---|
| Tetrahydrozoline hydrochloride | 0.05 g |
| Lidocaine | 3 g |
| Hydrocortisone acetate | 0.5 g |
| Allantoin | 1 g |
| Carboxyvinyl polymer | 3 g |
| Liquid paraffin | 82.45 g |
| Dextrin fatty acid ester | 10 g |

Production Process

An ointment base (liquid paraffin and dextrin fatty acid ester) heated and melted (70° C.–90° C.) was cooled to about 60° C. and thereafter mixed with the other components with stirring to obtain an injection type ointment.

EXAMPLE 8
Composition

| | |
|---|---|
| Naphazoline hydrochloride | 0.05 g |
| Lidocaine | 3 g |
| Prednisolone acetate | 0.1 g |
| Allantoin | 1 g |
| Carboxyvinyl polymer | 3 g |
| White vaseline | 92.85 g |

Production Process

An ointment base (vaseline) was heated and melted (70° C.–90° C.), was mixed with the other components with stirring and thereafter the mixture was cooled to about 40° C. to obtain an injection type ointment.

COMPARATIVE EXAMPLE 1

In the same manner as in Example 1, the production process was conducted using the same composition as in Example 1, except that the tetrahydrozoline hydrochloride was omitted and replaced with a suppository base (Witepsol W35) in an amount equal thereto.

COMPARATIVE EXAMPLE 2

In the same manner as in Example 1, the production process was conducted using the same composition as in Example 1, except that the carboxyvinyl polymer was omitted and replaced with an ointment base (Witepsol W35) in an amount equal thereto.

COMPARATIVE EXAMPLE 3

In the same manner as in Example 1, the production process was conducted using the same composition as in Example 1, except that the tetrahydrozoline hydrochloride and the carboxyvinyl polymer were omitted and replaced with a suppository base (Witepsol W35) in an amount equal thereto.

TEST EXAMPLE 1
Determination of Amount of Drug in Rectal Tissue
Specimen

The suppository of Example 1 was used as a specimen. As control specimens, the suppositories of Comparative Examples 1 to 3 were used.

Test Method

As the test method, the durability-in-rectum test in "Clinical Report", Vol. 42, No. 8, pages 1618–1626 (1993) was followed. After fasting for 48 hours, to each of male Japanese white house rabbits (body weight: 2.5–3.0 kg), which were arbitrarily divided into groups each consisting of 5 rabbits, was administered the specimen or control specimen, and immediately the anal region was closed with Aronaipha to prevent the suppository from leaking. After the lapse of the given period of time, the rectum was enucleated and sufficiently washed with physiological saline, after which a rectal tissue of a section of 10 cm from the anal region was taken. The tissue taken was homogenated in 20 ml of purified water, and the drug was extracted from 2 ml thereof with 10 ml of dichloromethane, after which 8 ml thereof was evaporated to dryness. Thereto was added 1 ml of methanol to well dissolve the residue therein to prepare a sample solution, and this sample solution was subjected to high-performance liquid chromatography (HPLC) to determine the amounts of lidocaine and hydrocortisone acetate contained in 1 g of the affected tissue in the rectum. The enucleation of rectum was conducted after 30 minutes, one hour, three hours and six hours from the administration.

Result

Figure 2:
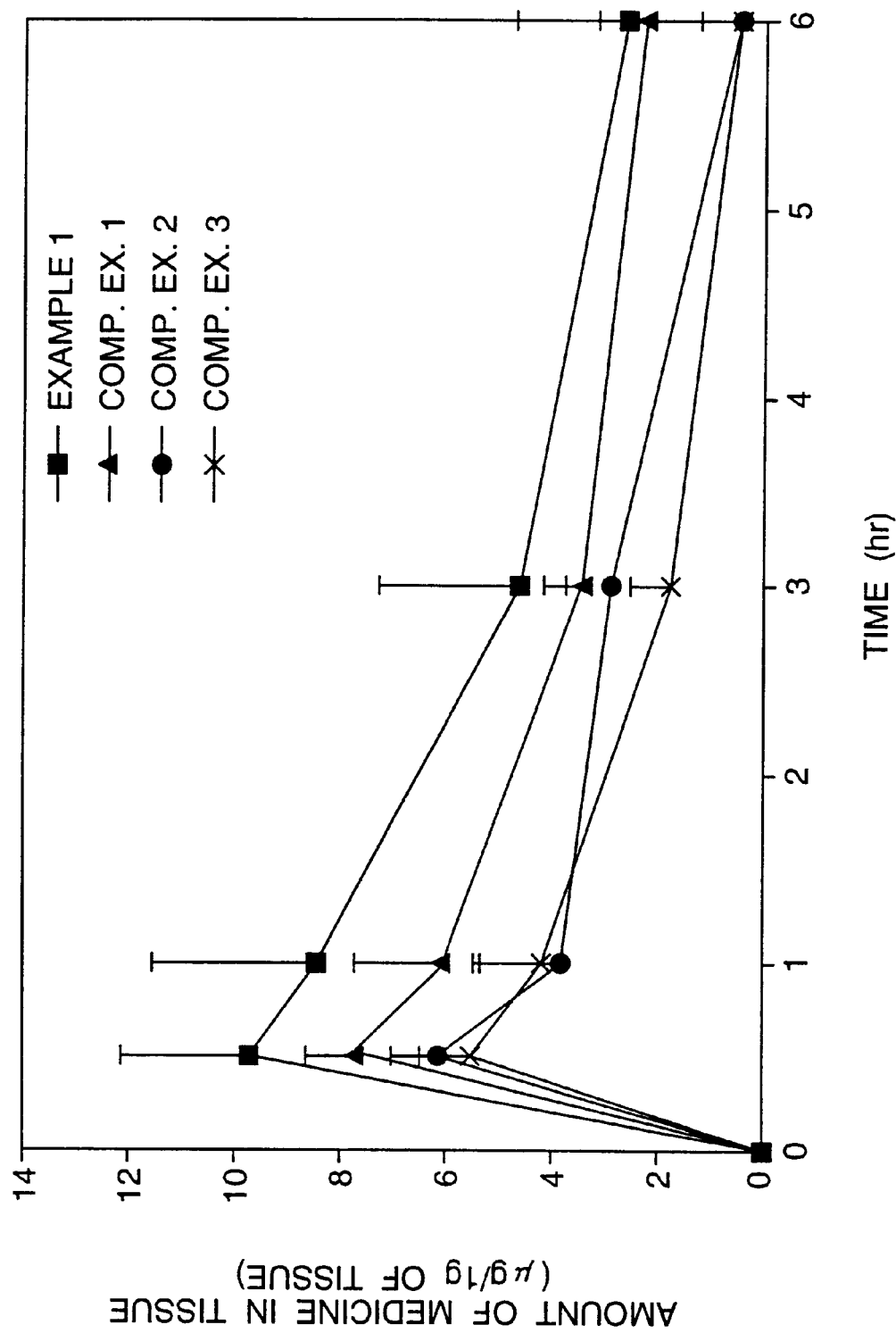
FIG. 2 is a graph showing the results of determination of the amount of hydrocortisone acetate in 1 g of rectal tissue of a section of 10 cm from the anal region.

When the specimen was compared with the control specimen, the former was larger in the amount of the former medicine was found to be larger in the rectal tissue than the latter. The results of the determination of the amount of lidocaine in the rectal tissue are shown in FIG. 1 and the results of the determination of the amount of hydrocortisone acetate are shown in FIG. 2.

TEST EXAMPLE 2
Edema Inhibition Test
Specimen

The suppository of Example 1 was used as a specimen. As control specimens, the suppositories of Comparative Examples 1 and 3 were used.

Test Method

The test method was in accordance with "Basic and Clinical Report", 27 (6), pages 2053–2062 (1993). After fasting for 24 hours, into the anal regions of male Wister rats (body weight: 150–170 g), which were arbitrarily divided to groups each consisting of 12 rats, was inserted a swab impregnated with 0.16 ml of a prophiogistic agent (6% croton oil solution in ether distilled water:pyridine:ether =10:1:4:5) for 10 seconds to cause inflammation and immediately the specimen or the control specimen (in each case, the diameter was 3 mm and the length was 10 mm per 100 g of weight) was administered to each of the rats. After the administration of the suppository, the anal region was closed with a clip to prevent the suppository from leaking. After the lapse of six hours, the rectum was enucleated and an affected rectal tissue of a section of 5–20 mm from the anal region was taken. The wet weight thereof was measured and the rectal anal coefficient (RAC) was calculated and used as an index of the degree of edema. Moreover, the edema inhibition percentage was calculated from the mean value of RAC obtained. RAC and edema inhibition percentage were calculated according to the following equation:

$$RAC = \frac{\text{Wet weight of rectal anal region (g)}}{\text{Body weight (g)}} \times 1000$$

Edema inhibition percentage (%)=[1−(RAC of suppository administered group−RAC of untreated administered group)/(RAC of prophlogistic control material administered group−RAC of untreated control group)]×100.

Result

When the specimen was compared with the control specimen, the former was found to have provided at least 2 times higher an edema inhibition percentage than the latter. The results thereof are shown in Table 1.

TABLE 1

| Administered group | Rectal anal co-efficient (RAC) | Edema inhibition (%) |
|---|---|---|
| Untreated | 0.82 ± 0.01 | — |
| Prophlogistic control material | 1.78 ± 0.06 | — |
| Example 1 | 1.14 ± 0.05 | 66.7 |
| Comparative Example 1 | 1.46 ± 0.04 | 33.3 |
| Comparative Example 3 | 1.66 ± 0.08 | 12.5 |

What is claimed is:

1. A long active composition for rectal administration which comprises an acrylic acid polymer, a vasoconstrictor and a rectal tissue-curing agent.

2. The composition for rectal administration according to claim 1, wherein the acrylic acid polymer is carboxyvinyl polymer.

3. The composition for rectal administration according to claim 1, wherein the vasoconstrictor is at least one member selected from the group consisting of tetrahydrozoline hydrochloride, naphazoline hydrochloride and oxymetazoline hydrochloride.

4. A long active suppository which comprises an acrylic acid polymer, a vasoconstrictor and a rectal tissue-curing agent.

* * * * *